United States Patent
Yeh

(10) Patent No.: US 9,891,180 B2
(45) Date of Patent: Feb. 13, 2018

(54) THERMAL NEEDLE PROBE

(71) Applicant: INDUSTRIAL TECHNOLOGY RESEARCH INSTITUTE, Hsinchu (TW)

(72) Inventor: Chien-Chih Yeh, Changhua County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 261 days.

(21) Appl. No.: 14/843,990

(22) Filed: Sep. 2, 2015

(65) Prior Publication Data

US 2017/0059498 A1  Mar. 2, 2017

(51) Int. Cl.
*G01N 25/18* (2006.01)
*G01K 3/10* (2006.01)

(52) U.S. Cl.
CPC ............... *G01N 25/18* (2013.01); *G01K 3/10* (2013.01)

(58) Field of Classification Search
None
See application file for complete search history.

(56) References Cited

U.S. PATENT DOCUMENTS

| | | | |
|---|---|---|---|
| 4,344,315 A | 8/1982 | Moxon et al. | |
| 5,115,127 A * | 5/1992 | Bobb | G01N 25/18 250/227.19 |
| 6,182,666 B1 | 2/2001 | Dobak, III | |
| 8,220,989 B1 | 7/2012 | Miller et al. | |
| 2006/0191344 A1* | 8/2006 | Hashimoto | A61B 8/00 73/632 |
| 2009/0124972 A1* | 5/2009 | Fischer | A61B 18/02 604/113 |
| 2013/0044788 A1* | 2/2013 | Snyder | G01K 7/02 374/179 |

FOREIGN PATENT DOCUMENTS

| | | |
|---|---|---|
| CN | 101803947 A | 8/2010 |
| CN | 101755196 B | 12/2011 |
| CN | 202994698 U | 6/2013 |
| CN | 102949237 B | 12/2014 |

(Continued)

OTHER PUBLICATIONS

Taiwanese Office Action dated Jul. 5, 2016.

(Continued)

*Primary Examiner* — Erica Lin
(74) *Attorney, Agent, or Firm* — Rabin & Berdo, P.C.

(57) ABSTRACT

According to embodiments of the disclosure, a thermal needle probe is provided. The thermal needle probe may include a heater, a cooler, a temperature measuring element, a heat conduction element and a processor. The heater is configured to heat an object. The cooler is configured to cool the object. The temperature measuring element is configured to measure a temperature raising curve of the object and a temperature dropping curve of the object. The heat conduction element is configured to conduct heat between the heater and the object. The processor is configured to determine a thermal property of the object according to at least one of the temperature raising curve and the temperature dropping curve.

17 Claims, 2 Drawing Sheets

(56) References Cited

FOREIGN PATENT DOCUMENTS

| JP | 2009-145204 A | 7/2009 |
|---|---|---|
| TW | 585252 U | 4/2004 |
| TW | 201025497 A | 7/2010 |
| TW | I436010 B | 5/2014 |

OTHER PUBLICATIONS

Continuous heat probe method for thermal conductivity measurement and analysis of buffer material, Ta-Yu Chang, 2004, thesis of Department of Civil Engineering of National Central University.
Error analysis of thermal probe method for measuring thermal conductivity of rocks, I-Chan Chung et al., 2012 Taiwan Rock Engineering Symposium, Miaoli, Taiwan Reference3: The study of measuring the thermal conductivity of geotechnical materials with thermal probe method, Yong-Ming Tien et al., 2006 Taiwan Rock Engineering Symposium, Tainan.
2006 Taiwan Rock Engineering Symposium, Tainan, Jun. 26-27.
W.J. Batty et al., "Assessment of the Themal-probe Technique for Rapid, Accurate Measurements of Effective Thermal Conductivities", 1984.
"Standard Test Method for Determination of Thermal Conductivity of Soil and Soft Rock by Thermal Needle Probe Procedure1", Aug. 2000.
Aaron P. Zent et al., "Thermal and Electrical Conductivity Probe (TECP) for Phoenix", Journal of Geophysical Research, vol. 114, 2009.

\* cited by examiner

THERMAL NEEDLE PROBE

TECHNICAL FIELD

The disclosure relates in general to a thermal needle probe having temperature measuring element.

BACKGROUND

Although conventional steady-state hot plate method or heat flow meter method can accurately and directly measure thermal conductivity of an object, however, it is inefficient because of the sample is required to be large and several hours may be needed for measuring.

SUMMARY

According to one embodiment of the disclosure provides a thermal needle probe. The thermal needle probe may include a heater, a cooler, a temperature measuring element, a heat conduction element and a processor. The heater is configured to heat an object. The cooler is configured to cool the object. The temperature measuring element is configured to measure a temperature raising curve of the object and a temperature dropping curve of the object. The heat conduction element is configured to conduct heat between the heater and the object. The processor is configured to determine a thermal property of the object according to at least one of the temperature raising curve and the temperature dropping curve.

The above and other aspects of the disclosure will become better understood with regard to the following detailed description of the non-limiting embodiment(s). The following description is made with reference to the accompanying drawings.

Figure 1:
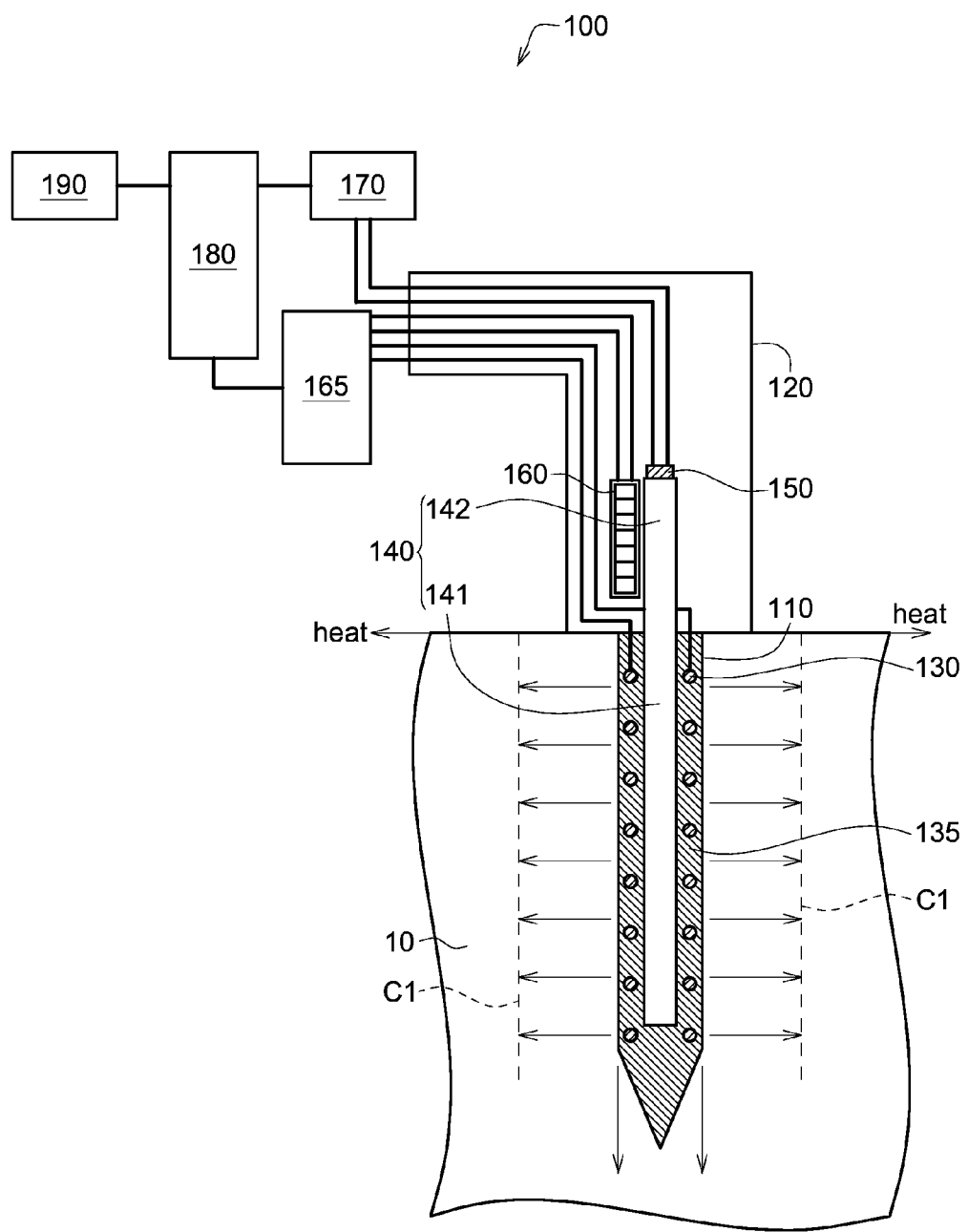
FIG. 1 illustrates a diagram of a thermal needle probe according to an embodiment of the disclosure.

In the following detailed description, for purposes of explanation, numerous details are set forth in order to provide a thorough understanding of the disclosed embodiments. It will be clear, that one or more embodiments may be practiced without these details. In other instances, well-known structures and devices are schematically shown in order to simplify the drawing.

DETAILED DESCRIPTION

Referring to FIG. 1, FIG. 1 illustrates a diagram of a thermal needle probe 100 according to an embodiment of the disclosure. The thermal needle probe 100 includes an insert portion 110, a non-insert portion 120, a heater 130, a filler 135, a heat conduction element 140, a temperature measuring element 150, a cooler 160, a power supply 165, an amplifier 170, a processor 180 and a display 190.

The insert portion 110 may insert an object 10 is configured to measure a thermal property of the object 10, such as thermal conductivity. The non-insert portion 120 connects to the insert portion 110 and is located outside the object 10 as the insert portion 110 inserts the object 10.

The heater 130 is, for example, a heat wire. The heater 130 may heat the object 10 is configured to measure the thermal property of the object 10. To stabilize the heater 130 and the heat conduction element 140, the filler 135 may encapsulate the heat conduction element 140 and the heater 130.

In an embodiment, the filler 135 is made of the material with low thermal conductivity, such as epoxy. Although the heater 130 is encapsulated by the filler 135 with low thermal conductivity, the heat generated for length of unit by the heater 130 still can be effectively conducted to the object 10 through the heat conduction element 140.

The heat conduction element 140 may conduct the heat between the heater and the object 10 uniformly and rapidly. In the present embodiment, the heat conduction element 140 is, for example, a heat pipe. The heat pipe has a high thermal conductivity, and thus may uniformly conduct the heat to the object 10. In detail, as shown in FIG. 1, the heat thermal conducting curve C1 presenting the heat from the insert portion 110 to the object approaches a line.

The heat conduction element 140 also may conduct the heat of the object 10 to the temperature measuring element 150, such that the temperature measuring element 150 may measure the temperature of the object 10, such as transient temperature and/or steady temperature. In addition, since the heat conduction element 140 merely conducts the heat without absorbing the heat, the measured temperature of the object 10 may be accurate. In an embodiment, the temperature measuring element 150 is, for example, a thermocouple, a thermistor, etc.

In addition, the heat conduction element 140 includes a first portion 141 and a second portion 142. The first portion 141 is disposed within the non-insert portion 120, and the second portion 142 is disposed within the insert portion 110.

The temperature measuring element 150 is disposed adjacent to the heat conduction element 140. For example, the temperature measuring element 140 is disposed adjacent to the non-insert portion 142. Since the heat conduction element 140 has a high thermal conductivity (for example, up to 5000 W/m-k), the temperature conducted in any point of the heat conduction element 140 are uniform, and accordingly the temperature measured by the temperature measuring element 150 can represent the exact temperature of the object 10. In the present embodiment, the temperature measuring element 150 may be disposed on one end of the heat conduction element 140. In another embodiment, the temperature measuring element 150 may be disposed on any portion of the heat conduction element 140, for example, any portion of the first portion 141 or any portion of the second portion 142.

The cooler 160 may cool the heater 130, such that the temperature of the object 10 drops. The dropped temperature of the object 10 may be measured by the temperature measuring element 150. In an embodiment, the cooler 160 is, for example, a thermoelectric cooling module (TEC).

The power supply 165 may be controlled by the processor 180 and provide the heater 130 and the cooler 160 with electricity.

The amplifier 170 may receive the voltage single of the temperature measured by the temperature measuring element 150 and amplify the voltage single if necessary. Then, the amplifier 170 may transmit the amplified voltage single to the processor 180.

The processor 180 may process the amplified voltage single to obtain the temperature of the object 10. The display 190 may display the temperature of the object 10.

Figure 2:
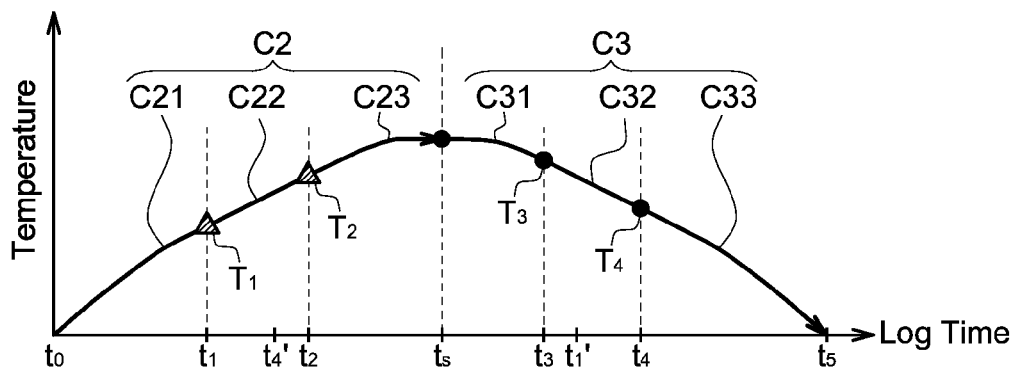
FIG. 2 illustrates a diagram of a temperature raising curve and a temperature dropping curve of the object measured by the thermal needle probe of FIG. 1.

FIG. 2 illustrates a diagram of a temperature raising curve C2 and a temperature dropping curve C3 of the object 10 measured by the thermal needle probe 100 of FIG. 1. The heat generated for length of unit by the heater 130 is conducted within the object 10, and the temperature measuring element 150 may measure the temperature raising curve C2 of the object 10 due to the heat conducting.

As shown in FIG. 2, the temperature raising curve C2 includes an initial transient curve C21 which is from $t_0$ to $t_1$, a raising linear segment C22 which is from $t_1$ to $t_2$ and a steady raising curve C23 which is from $t_2$ to $t_s$. Compared with the design of no heat conduction element 140, the initial transient curve C21 and the steady raising curve C23 may be shorter and the raising linear segment C22 is longer due to the high thermal conductivity of the heat conduction element 140. Furthermore, since the heater 130 may conduct the heat uniformly and rapidly, the initial transient curve C21 and the steady raising curve C23 may shorten, and the raising linear segment C22 may elongate.

The processor 180 may calculate the thermal conductivity of the object 10 according to a slope of the raising linear segment C22.

For example, as shown in equation (1) below, the thermal conductivity k1 of the object 10 may be calculated by the equation (1). In equation (1), Q (W/m) represents the heat generated for length of unit by the heater 130, $T_2$ represents the temperature of the object 10 at $t_2$ of the raising linear segment C22, and $T_1$ represents the temperature of the object 10 at $t_1$ of the raising linear segment C22.

$$k1 = \frac{Q}{4\pi(T_2 - T_1)} ln\left(\frac{t_2}{t_1}\right) \quad (1)$$

Since the thermal conductivity of the object 10 may be obtained before the steady state, such as the steady raising curve C23 and/or the initial transient curve C21 shorten, the calculating time of thermal conductivity and the required measuring time may reduce.

When the slope of the temperature raising curve C2 is less than a predetermined value, such as 0.5, at $t_s$, it presents the temperature raising curve C2 reaches steady state, and accordingly the processor 180 may control the cooler 160 to cool the object 10 and simultaneously control the heater 130 to stop heating the object 10. In another embodiment, when the variation of the slope of the temperature raising curve C2 is less than a predetermined value, it presents the temperature raising curve C2 reaches steady state, and accordingly the processor 180 may control the cooler 160 to cool the object 10 and simultaneously control the heater 130 to stop heating the object 10.

In some embodiment, the processor 180 may, using mathematical simulation technology, determine the regions of the initial transient curve C21, the raising linear segment C22 and the steady raising curve C23 during a predetermined time interval given by the processor 180. After the predetermined time interval of heating the object 10 lapses, the processor 180 controls the heater 130 to stop heating the object 10 and simultaneously control the cooler 160 to start cooling the object 10 until the temperature of the object 10 returning to the initial temperature, such as $t_0$.

As shown in FIG. 2, the temperature dropping curve C3 includes an initial steady curve C31 which is from $t_s$ to $t_3$, a dropping linear segment C32 which is from $t_3$ to $t_4$ and a transient dropping curve C33 which is from $t_4$ to $t_5$. Compared with the design of no heat conduction element 140, the initial steady curve C31 and the transient dropping curve C33 may be shorter and the dropping linear segment C32 is longer due to the high thermal conductivity of the heat conduction element 140. Furthermore, since the heater 130 may conduct the heat uniformly and rapidly, the initial steady curve C31 and the transient dropping curve C33 may shorten, and the dropping linear segment C32 may elongate.

The processor 180 may calculate the thermal conductivity of the object 10 according to a slope of the transient dropping curve C33.

For example, as shown in equation (2) below, the thermal conductivity k2 of the object 10 may be calculated by the equation (2). In equation (2), $T_3$ represents the temperature of the object 10 at $t_3$ of the transient dropping curve C33, and $T_4$ represents the temperature of the object 10 at $t_4$ of the transient dropping curve C33.

$$k2 = \frac{Q}{4\pi(T_3 - T_4)} ln\left(\frac{t_4}{t_3}\right) \quad (2)$$

In an embodiment, the thermal conductivity k2 of the object 10 may be equal to or different from the thermal conductivity k1 of the object 10. If the thermal conductivity k2 of the object 10 is different from the thermal conductivity k1 of the object 10, the processor 180 may calculate an average of the thermal conductivity k1 and k2.

Figure 3:
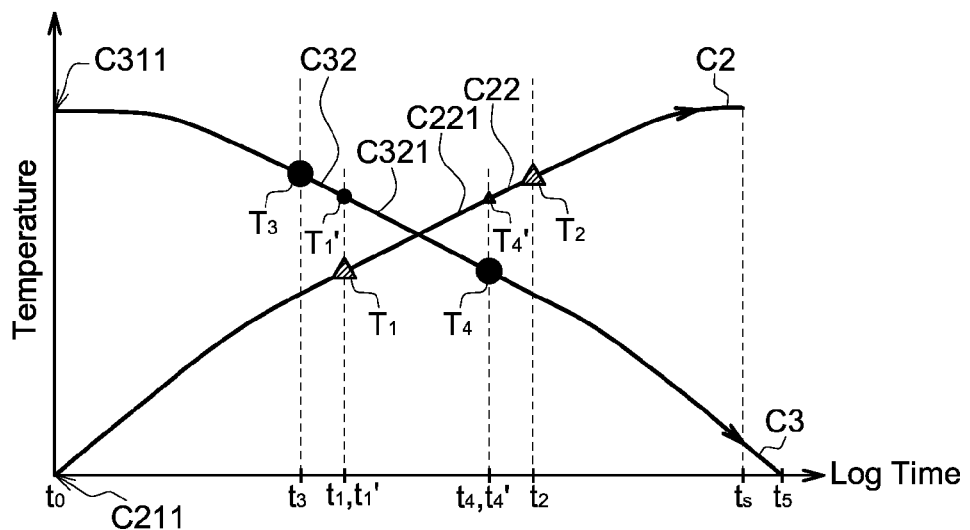
FIG. 3 illustrates a diagram of the temperature raising curve and the temperature dropping curve of FIG. 2 overlapping.

Referring to FIG. 3, FIG. 3 illustrates a diagram of the temperature raising curve C2 and the temperature dropping curve C3 of FIG. 2 overlapping. The temperature dropping curve C3 is shifted to overlap the temperature raising curve C2. For example, the terminal C311 of the temperature dropping curve C3 corresponding to $t_s$ may overlap the terminal C211 of the temperature raising curve C2 corresponding to $t_0$.

The processor 180 may determine the thermal property of the object 10 according to the temperature raising curve C2 and the temperature dropping curve C3.

For example, as shown in FIG. 3, the processor 180 may determine a first overlapping curve C221 of the raising linear segment C22 which overlap the dropping linear segment C32 and calculate a slope of the first overlapping curve C221. In detail, the first overlapping curve C221 which is form $t_1$ to $t_4$ overlaps the dropping linear segment C32, and the processor 180 may calculate the slope of the first overlapping curve C221. The slope of the first overlapping curve C221 represents the thermal property of the object 10, such as thermal conductivity.

For example, as shown in equation (3) below, the thermal conductivity k3 of the object 10 may be calculated by the equation (3). In equation (3), Q represents the heat generated for length of unit by the heater 130, $T_{4'}$ represents the temperature of the object 10 at $t_{4'}$ (as shown in FIG. 2) of the first overlapping curve C221 corresponding $t_4$, and $T_1$ represents the temperature of the object 10 at $t_1$ of the first overlapping curve C221.

$$k3 = \frac{Q}{4\pi(T_{4'} - T_1)} ln\left(\frac{t_{4'}}{t_1}\right) \quad (3)$$

Similarly, as shown in FIG. 3, the processor 180 may determine a second overlapping curve C321 of the dropping linear segment C32 which overlap the raising linear segment C22 and calculate a slope of the second overlapping curve C321. In detail, the second overlapping curve C321 which is form $t_1$ to $t_4$ overlaps the raising linear segment C22, and the processor 180 may calculate the slope of the second overlapping curve C321. The slope of the second overlapping curve C321 represents the thermal property of the object 10, such as thermal conductivity.

For example, as shown in equation (4) below, the thermal conductivity k4 of the object 10 may be calculated by the equation (4). In equation (4), $T_{1'}$ represents the temperature of the object 10 at $t_{1'}$ (as shown in FIG. 2) of the second overlapping curve C321 corresponding $t_1$, and $T_4$ represents the temperature of the object 10 at $t_4$ of the second overlapping curve C321.

$$k4 = \frac{Q}{4\pi(T_{1'} - T_4)} ln\left(\frac{t_4}{t_{1'}}\right) \qquad (4)$$

Since the first overlapping curve C221 and the second overlapping curve C321 overlap in linear region of the raising linear segment C22 and the dropping linear segment C32, the thermal conductivity k1 and the thermal conductivity k2 are substantially equal. In addition, since the overlapping of the raising linear segment C22 and the dropping linear segment C32, the accurate of the slope may increase, and accordingly the accurate of the thermal conductivity of the object 10 may increase.

It will be clear that various modifications and variations can be made to the disclosed embodiments. It is intended that the specification and examples be considered as exemplary only, with a true scope of the disclosure being indicated by the following claims and their equivalents.

What is claimed is:

1. A thermal needle probe, comprising:
   a heater configured to heat an object;
   a cooler configured to cool the object;
   a temperature measuring element configured to measure a temperature raising curve of the object and a temperature dropping curve of the object;
   a heat conduction element configured to conduct heat between the heater and the object; and
   a processor configured to determine a thermal property of the object according to at least one of the temperature raising curve and the temperature dropping curve;
   wherein the thermal needle probe further comprises an insert portion configured to be inserted into the object, and the heater is disposed on the insert portion.

2. The thermal needle probe according to claim 1, wherein the heat conduction element is a heat pipe.

3. The thermal needle probe according to claim 1, wherein the cooler is a thermoelectric cooling module (TEC).

4. The thermal needle probe according to claim 1, wherein the temperature measuring element is a thermocouple.

5. The thermal needle probe according to claim 1, wherein the temperature measuring element is disposed adjacent to the heat conduction element.

6. The thermal needle probe according to claim 1, comprising:
   a non-insert portion connecting to the insert portion;
   wherein a portion of the heat conduction element is disposed within the non-insert portion, and another portion of the heat conduction element is disposed within the insert portion.

7. The thermal needle probe according to claim 6, wherein the temperature measuring element is disposed adjacent to the non-insert portion.

8. The thermal needle probe according to claim 1, wherein the temperature raising curve has a raising linear segment, and the processor is configured to calculate a slope of the raising linear segment.

9. The thermal needle probe according to claim 1, wherein the temperature dropping curve has a dropping linear segment, and the processor is configured to calculate a slope of the dropping linear segment.

10. The thermal needle probe according to claim 1, wherein the temperature raising curve has a raising linear segment, the temperature dropping curve has a dropping linear segment, and the processor is configured to determine a first overlapping curve of the raising linear segment which overlap the dropping linear segment and calculate a slope of the first overlapping curve.

11. The thermal needle probe according to claim 1, wherein the temperature raising curve has a raising linear segment, the temperature dropping curve has a dropping linear segment, and the processor is configured to determine a second overlapping curve of the dropping linear segment which overlap the raising linear segment and calculate a slope of the second overlapping curve.

12. The thermal needle probe according to claim 1, wherein the temperature raising curve has a raising linear segment, the temperature dropping curve has a dropping linear segment, and the processor is configured to determine a first overlapping curve of the raising linear segment which overlaps the dropping linear segment, determine a second overlapping curve of the dropping linear segment which overlap the raising linear segment and calculate an average slope of the first overlapping curve and the second overlapping curve.

13. The thermal needle probe according to claim 1, wherein the processor is configured to control the cooler to cool the object and control the heater to stop heating the object as a slope or a variation of the slope of the temperature raising curve is less than a predetermined value.

14. The thermal needle probe according to claim 13, wherein the processor is configured to control the heater to stop heating the object as the cooler starts to cool the object.

15. The thermal needle probe according to claim 1, further comprising:
   a filler encapsulating the heat conduction element and the heater.

16. The thermal needle probe according to claim 1, wherein the thermal property is thermal conductivity.

17. The thermal needle probe according to claim 1, wherein the temperature raising curve comprises an initial transient curve, a raising linear segment and a steady raising curve, and the processor is configured to determine regions of the initial transient curve, the raising linear segment and the steady raising curve during a predetermined time interval, and after the predetermined time interval of heating the object lapses, the processor is configured to control the heater to stop heating the object and simultaneously control the cooler to start cooling the object.

* * * * *